United States Patent
Nakaoka et al.

(10) Patent No.: US 8,313,426 B2
(45) Date of Patent: Nov. 20, 2012

(54) ENDOSCOPE SYSTEM

(75) Inventors: Masaya Nakaoka, Tokyo (JP); Koki Morishita, Tokyo (JP)

(73) Assignee: Olympus Corporation, Tokyo (JP)

( * ) Notice: Subject to any disclaimer, the term of this patent is extended or adjusted under 35 U.S.C. 154(b) by 818 days.

(21) Appl. No.: 12/521,224

(22) PCT Filed: Nov. 26, 2007

(86) PCT No.: PCT/JP2007/072725
§ 371 (c)(1), (2), (4) Date: Jun. 25, 2009

(87) PCT Pub. No.: WO2008/081659
PCT Pub. Date: Jul. 10, 2008

(65) Prior Publication Data
US 2010/0094136 A1 Apr. 15, 2010

(30) Foreign Application Priority Data
Dec. 28, 2006 (JP) .................................. 2006-356139

(51) Int. Cl.
*A61B 1/06* (2006.01)
(52) U.S. Cl. ........................................ 600/160; 600/178
(58) Field of Classification Search .................. 600/103, 600/160, 178, 181; 362/574; 348/68–70
See application file for complete search history.

(56) References Cited

U.S. PATENT DOCUMENTS
5,749,830 A * 5/1998 Kaneko et al. ................ 600/160
5,833,617 A 11/1998 Hayashi
(Continued)

FOREIGN PATENT DOCUMENTS
JE 2001-137173 5/2001
(Continued)

OTHER PUBLICATIONS
Zimmermann, T. et al., "Spectral imaging and its applications in live cell microscopy", *FEBS Letters*, (2003), vol. 546, No. 1, pp. 87-92.
(Continued)

*Primary Examiner* — Philip R Smith
(74) *Attorney, Agent, or Firm* — Scully Scott Murphy & Presser, PC

(57) ABSTRACT

A fluorescence distribution image of each fluorescent agent can be acquired from a fluorescence image that has been captured in a mixed state so as to improve the diagnosability of cancer cells. An endoscope system comprises: a light source section for selectively irradiating two or more types of excitation lights having different spectral characteristics so as to excite two or more types of fluorescent agents having different optical characteristics; an imaging section provided on a part to be inserted into a body cavity, and having a light-receiving sensitivity in the wavelength bands of the two or more types of fluorescence radiated from the observation target by respective types of excitation lights; a storage section for storing relation information between the fluorescence intensity and the concentration of each of the fluorescent agents; a concentration information computing section for computing concentration information of each of the fluorescent agents on the basis of the fluorescence intensities of two or more images captured by the imaging section and the relation information stored in the storage section, and outputting the concentration information; and a mode switching section capable of switching between a first fluorescence observation mode in which at least one of the fluorescence intensity images acquired by the imaging section is presented, and a second fluorescence observation mode in which the concentration information of each of the florescent agents computed by the concentration information computing section is presented.

6 Claims, 6 Drawing Sheets

U.S. PATENT DOCUMENTS

| | | | |
|---|---|---|---|
| 7,341,557 B2 * | 3/2008 | Cline et al. | 600/160 |
| 7,857,751 B2 * | 12/2010 | Iketani et al. | 600/109 |
| 2002/0026099 A1 * | 2/2002 | Adachi et al. | 600/178 |
| 2002/0161282 A1 * | 10/2002 | Fulghum | 600/160 |
| 2005/0027166 A1 | 2/2005 | Matsumoto et al. | |
| 2006/0020169 A1 * | 1/2006 | Sugimoto | 600/180 |
| 2006/0052710 A1 | 3/2006 | Miura et al. | |
| 2006/0173240 A1 * | 8/2006 | Fukuyama et al. | 600/118 |
| 2006/0173358 A1 * | 8/2006 | Xie | 600/476 |
| 2007/0016077 A1 | 1/2007 | Nakaoka et al. | |
| 2007/0046778 A1 * | 3/2007 | Ishihara et al. | 348/68 |
| 2007/0100207 A1 * | 5/2007 | Ueno et al. | 600/160 |

FOREIGN PATENT DOCUMENTS

| | | |
|---|---|---|
| JP | 9-308604 | 12/1997 |
| JP | Hei 10-201707 | 8/1998 |
| JP | 2006-25802 | 2/2006 |
| JP | 2006-187598 | 7/2006 |

OTHER PUBLICATIONS

European Search Report in connection with Application No. EP 07 83 2450, (Apr. 1, 2011).

* cited by examiner

ENDOSCOPE SYSTEM

TECHNICAL FIELD

The present invention relates to an endoscope system.

BACKGROUND ART

Conventionally, it is known that some types of proteins etc. are overexpressed in cancer cells, as compared to in normal sites. A method has been proposed in which a fluorescent probe is used to make thus expressed proteins or other molecules luminous to thereby diagnose cancer cells, as well as observing this fluorescence in an endoscopic manner to thereby identify these cancer cells (for example, refer to Patent Document 1).

In Patent Document 1, an endoscope apparatus in which a single type of fluorescent probe is used for diagnosing cancer cells, has been disclosed.

Patent Document 1:

Japanese Unexamined Patent Application, Publication No. Hei 10-201707

DISCLOSURE OF INVENTION

However, even in non-cancerous sites such as a site of inflammation occurrence do exist molecules expressed by cancer cells, which may emit similar fluorescence. Therefore, the diagnosability for specifying cancer cells tends to be low only with a single type of fluorescent probe.

Meanwhile, it is known that not only a single type of molecule but also a plurality of types of molecules are expressed by cancer cells. The diagnosability can be improved by making these plurality of types of cancer cell-related molecules luminous with fluorescent dyes having respectively different optical characteristics, and observing them.

Fluorescence generated by excitation of a fluorescent agent is very weak, and thus is desirably captured in a wide wavelength band when a plurality of types of fluorescent agents are to be used for observation. When two or more types of fluorescent agents are used, the wavelength bands of their fluorescence tend to be overlapped. Therefore, it is difficult to obtain the distribution image of each fluorescent agent.

The present invention provides an endoscope system with which a fluorescence distribution image of each fluorescent agent can be acquired from a fluorescence image that has been captured in a mixed state, without using a special apparatus such as a variable spectral element, and the diagnosability of cancer cells can be improved.

The present invention provides an endoscope system at least a part of which can be inserted into a body cavity of an organism for capturing an image of an observation target in the body cavity, comprising: a light source section for selectively irradiating two or more types of excitation lights having different spectral characteristics so as to excite two or more types of fluorescent agents having different optical characteristics; an imaging section provided on the part to be inserted into the body cavity, having a filter which cuts the respective excitation lights, and having a light-receiving sensitivity in the wavelength bands of the two or more types of fluorescence radiated from the observation target by the respective excitation lights; a storage section for storing relation information between the fluorescence intensity generated by excitation with each of the excitation lights and the concentration of each of the fluorescent agents; a concentration information computing section for computing concentration information of each of the fluorescent agents on the basis of the fluorescence intensities of two or more images captured by the imaging section and the relation information stored in the storage section, and outputting the concentration information; and a mode switching section capable of switching between a first fluorescence observation mode in which at least one of the fluorescence intensity images acquired by the imaging section is presented, and a second fluorescence observation mode in which the concentration information of each of the fluorescent agents computed by the concentration information computing section is presented.

In the above invention, the mode switching section may switch the observation mode to the first fluorescence observation mode prior to the second fluorescence observation mode.

In the above invention, the relation information may be information on a ratio between the fluorescence intensity generated by excitation with each of the excitation lights and the concentration of each of the fluorescent agents.

In the above invention, the structure may also comprise a display section for displaying the concentration information that has been computed and output by the concentration information computing section.

In addition, in the above structure, the display section may also comprise a plurality of channels corresponding to display colors, and the concentration information corresponding to each of the fluorescent agents is allocated to each channel to be output.

In the above invention, the wavelengths of the respective excitation lights are set on the longer wavelength side than the near infrared region.

According to the present invention, a fluorescence distribution image of each fluorescent agent can be acquired from a fluorescence image that has been captured in a mixed-color state, without using a special apparatus such as a variable spectral element, and the diagnosability of cancer cells can be improved.

EXPLANATION OF REFERENCE SIGNS

1: Endoscope system
4: Light source unit (light source section)
7: Display unit (display section)
14: Imaging device (imaging section)

18: Image processing circuit (storage section, concentration information computing section)
N1 and N2: Concentration information

BEST MODE FOR CARRYING OUT THE INVENTION

Hereunder is a description of an endoscope system 1 according to a first embodiment of the present invention, with reference to FIG. 1 to FIG. 5.

Figure 1:
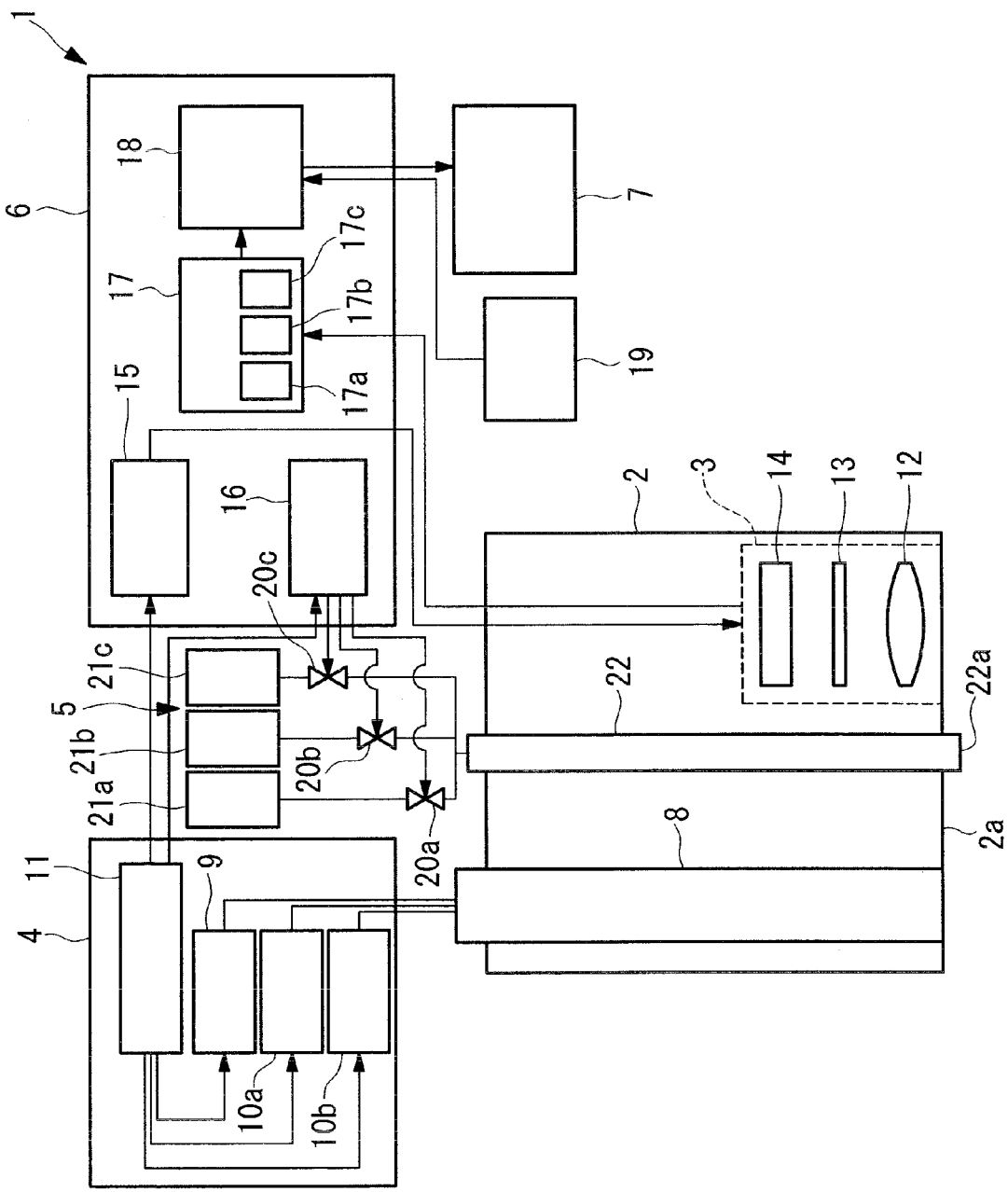
FIG. 1 is a block diagram showing the overall structure of an endoscope system according to a first embodiment of the present invention.

As shown in FIG. 1, the endoscope system 1 according to this embodiment comprises an insertion section 2 to be inserted into a body cavity of an organism, an imaging unit (imaging section) 3 disposed in the insertion section 2, a light source unit (light source section) 4 for emitting excitation light and illumination light for normal light observation, a liquid delivery unit 5 for supplying a liquid to be discharged from the distal end 2a of the insertion section 2, a control unit 6 for controlling the imaging unit 3, the light source unit 4, and the liquid delivery unit 5, and a display unit (display section) 7 for displaying the image captured by the imaging unit 3.

The insertion section 2 has an extremely narrow outer dimension to be insertable into a body cavity of an organism, and comprises therein a light guide 8 for transmitting light from the imaging unit 3 and the light source unit 4 to the distal end 2a.

The light source unit 4 comprises an illumination light source (light source section) 9 for emitting illumination light which illuminates the observation target in the body cavity so as to capture the reflected light that has been reflected by and returning from the observation target, two excitation light sources (light source section) 10a and 10b for emitting two types of excitation lights which are to be irradiated on the observation target in the body cavity to excite fluorescent substances existing in the observation target so as to generate fluorescence, and a light source controlling circuit (light source control section) 11 for controlling these light sources 9, 10a, and 10b.

The illumination light source 9 is, for example, a combination of a xenon lamp (not shown) and serially-switchable color filters so that red (R), green (G), and blue (B) illumination lights can be serially generated.

The excitation light source 10a is, for example, a semiconductor laser for emitting first excitation light having a peak wavelength of 680±5 nm. This first excitation light is capable of exciting an AlexaFluor (trademark) 680 (made by MolecularProbes)-based fluorescent probe. In addition, the excitation light source 10b is, for example, a semiconductor laser for emitting second excitation light having a peak wavelength of 700±5 nm. This second excitation light is capable of exciting an AlexaFluor (trademark) 700 (made by MolecularProbes)-based fluorescent probe.

Figure 2:
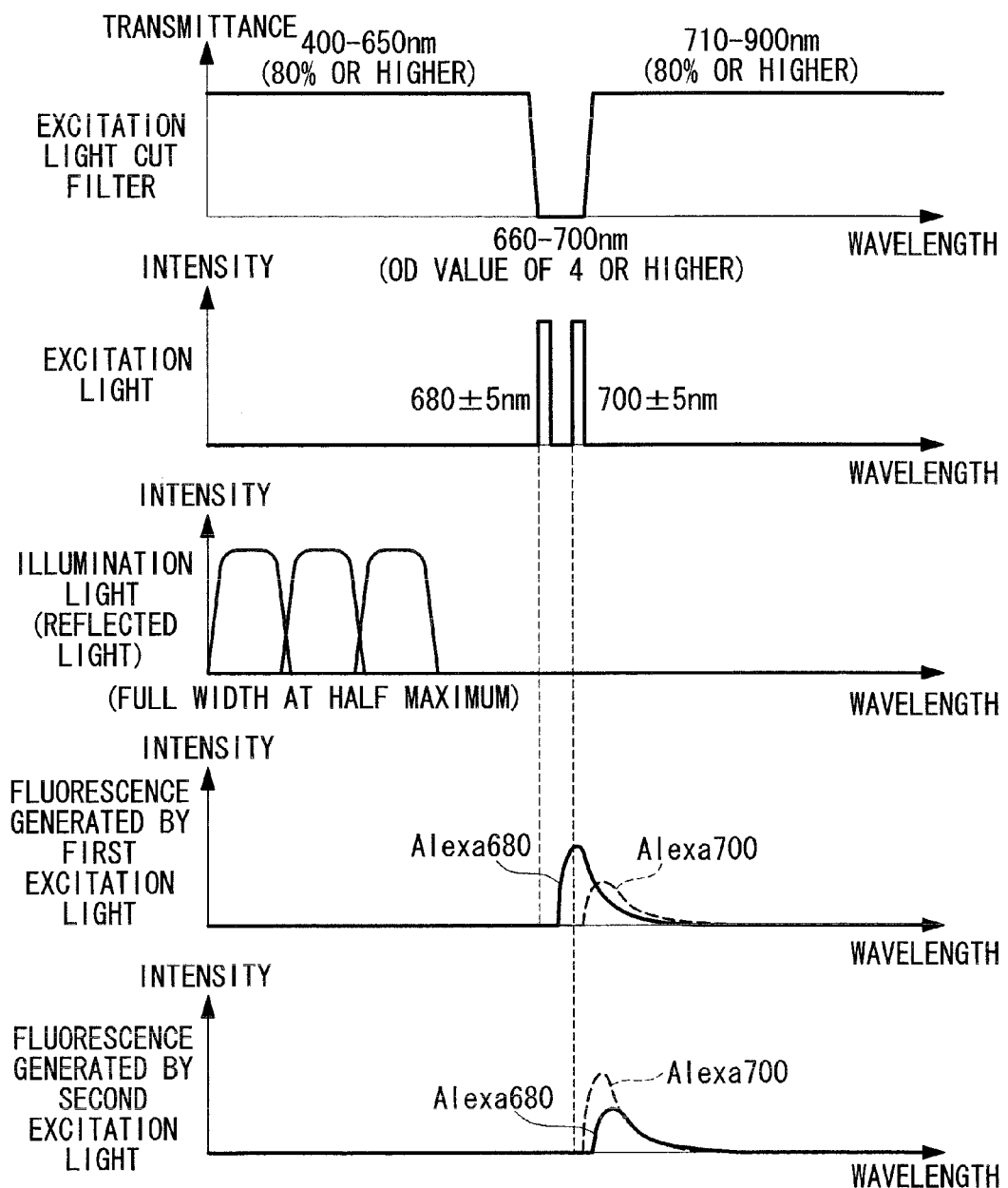
FIG. 2 shows the wavelength characteristics of the excitation light cut filter used for the endoscope system of FIG. 1, excitation light, illumination light, and fluorescence generated by excitation light.

As shown in FIG. 2, the wavelength bands of fluorescence generated by excitation of AlexaFluor (trademark) 680 and AlexaFluor (trademark) 700 are overlapped. For this reason, when the observation target is irradiated with either one of the first excitation light and the second excitation light in a state where these two fluorescent probes are spread over the observation target, these two fluorescent probes are simultaneously excited so that two different types of fluorescence are simultaneously generated.

The light source controlling circuit 11 is designed to alternatively turn on and off the illumination light source 9 and the excitation light sources 10a and 10b at predetermined timings according to the timing chart that will be described later.

The imaging unit 3 comprises an imaging optical system 12 for condensing light being incident from the observation target, an excitation light cut filter 13 for blocking excitation light being incident from the observation target, and an imaging device (imaging section) 14 for capturing light that has been condensed by the imaging optical system 12 and converting the light into an electric signal. As for the imaging device 14, there is employed a device having a light-receiving sensitivity over a wide wavelength band of not less than 400 nm and not more than 900 nm.

The excitation light cut filter 13 has a transmittance characteristic in which the transmittance is 80% or higher in a wavelength band of not less than 400 nm and not more than 650 nm, the OD value is 4 or higher (=transmittance of $1 \times 10^{-4}$ or lower) in a wavelength band of not less than 660 nm and not more than 700 nm, and the transmittance is 80% or higher in a wavelength band of not less than 710 nm and not more than 900 nm.

As shown in FIG. 1, the control unit 6 comprises an imager driving circuit (imager controlling circuit) 15 for drive-controlling the imager 14, a valve controlling circuit 16 that will be described later, a frame memory 17 for storing the image information acquired by the imager 14, and an image processing circuit (storage section, concentration information computing section) 18 for processing the image information stored in the frame memory 17 and outputting the processed image information to the display unit 7.

In addition, to the image processing circuit 18 is connected an input device 19.

The imaging device driving circuit 15 and the valve controlling circuit 16 are connected to the light source controlling circuit 11 so as to drive-control the imaging device 14 and valves 20a, 20b, and 20c synchronously with the switching operation between the illumination light source 9 and the excitation light sources 10a and 10b by the light source controlling circuit 11.

In addition, the present endoscope system has three observation modes: a normal light observation mode in which a reflected light image is presented; a screening fluorescence observation mode (first fluorescence observation mode) in which a fluorescence intensity image is presented; and an unmixing fluorescence observation mode (second fluorescence observation mode) in which the concentration distribution of a fluorescent agent obtained by computing the fluorescence intensity image is presented. An appropriate observation mode can be selected by the operation of a mode switching switch (mode switching section, not shown) by the user.

When the normal light observation mode is selected, the illumination light source 9 is always turned on, and the excitation light sources 10a and 10b are always turned off. The reflected lights of the red (R), green (G), and blue (B) illumination lights serially generated through the serially-switchable color filters can be stored in the frame memory 17 and output to respective channels of the display unit 7.

By so doing, the normal light image composed of the reflected lights of three R, G, and B colors can be taken.

Figure 3:
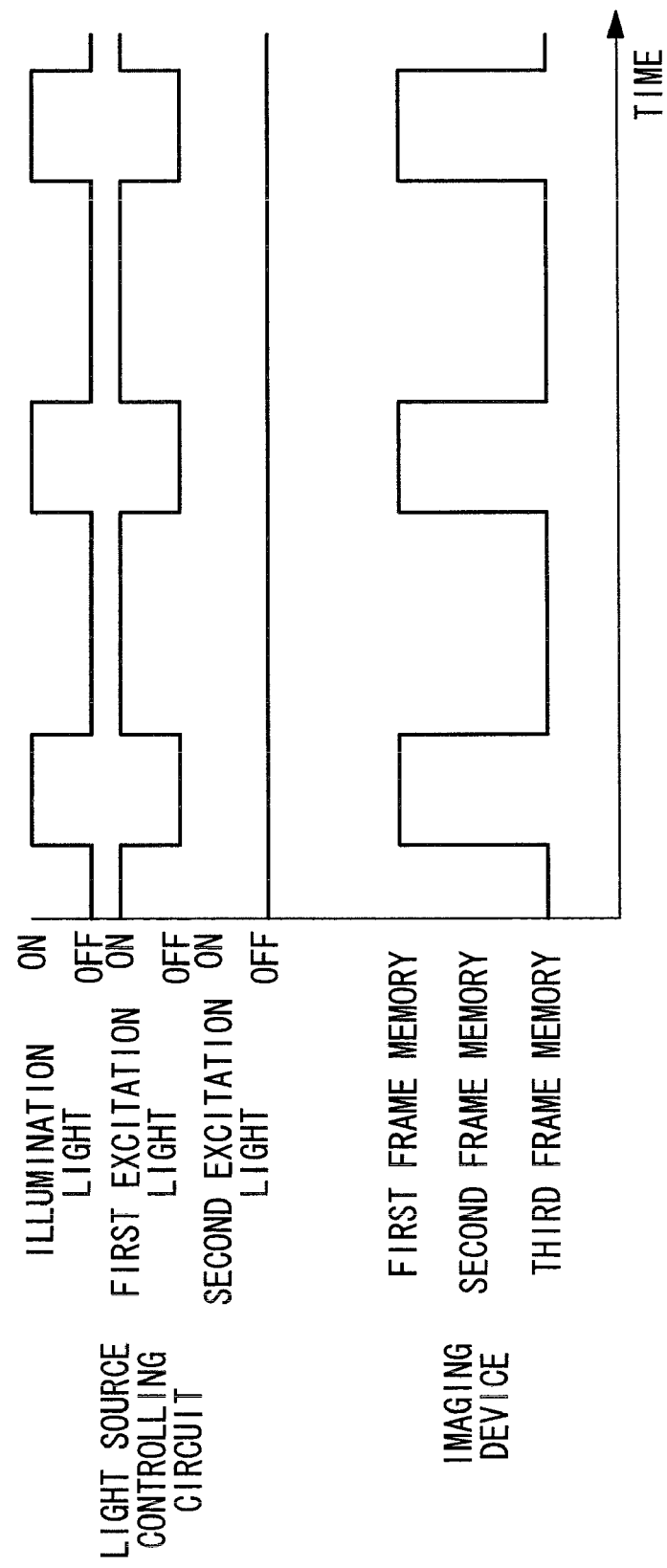
FIG. 3 is a timing chart for explaining the operation in the screening fluorescence observation mode of the endoscope system of FIG. 1.

When the screening fluorescence observation mode is selected, as shown in the timing chart of FIG. 3, by the operation of the light source controlling circuit 11, the excitation light source 10a and the illumination light source 9 are operated. When the excitation light is emitted from the excitation light source 10a, the imaging device driving circuit 15 outputs the image information, which has been output from the imaging device 14, to the first frame memory 17a.

In addition, when the illumination light is emitted from the illumination light source 9, the imaging device driving circuit 15 outputs the image information which has been output from the imaging device 14, to the third frame memory 17c. At this time, the blue (B) illumination light is irradiated as the illumination light by the operation of the color filter. On the other hand, excitation light is not emitted from the excitation light source 10b.

Moreover, the image processing circuit 18 receives the image information from the frame memory 17, and outputs the image information without a computation processing. For example, the fluorescence image that has been captured while the excitation light has been emitted from the excitation light source 10a, is received from the first frame memory 17a, and is output to the first (for example, red) channel of the display unit 7.

Furthermore, the image processing circuit 18 receives the reflected light image information acquired by irradiation of the blue illumination light, from the third frame memory 17c, and outputs the image information to the third (for example, blue) channel of the display unit 7.

Figure 4:
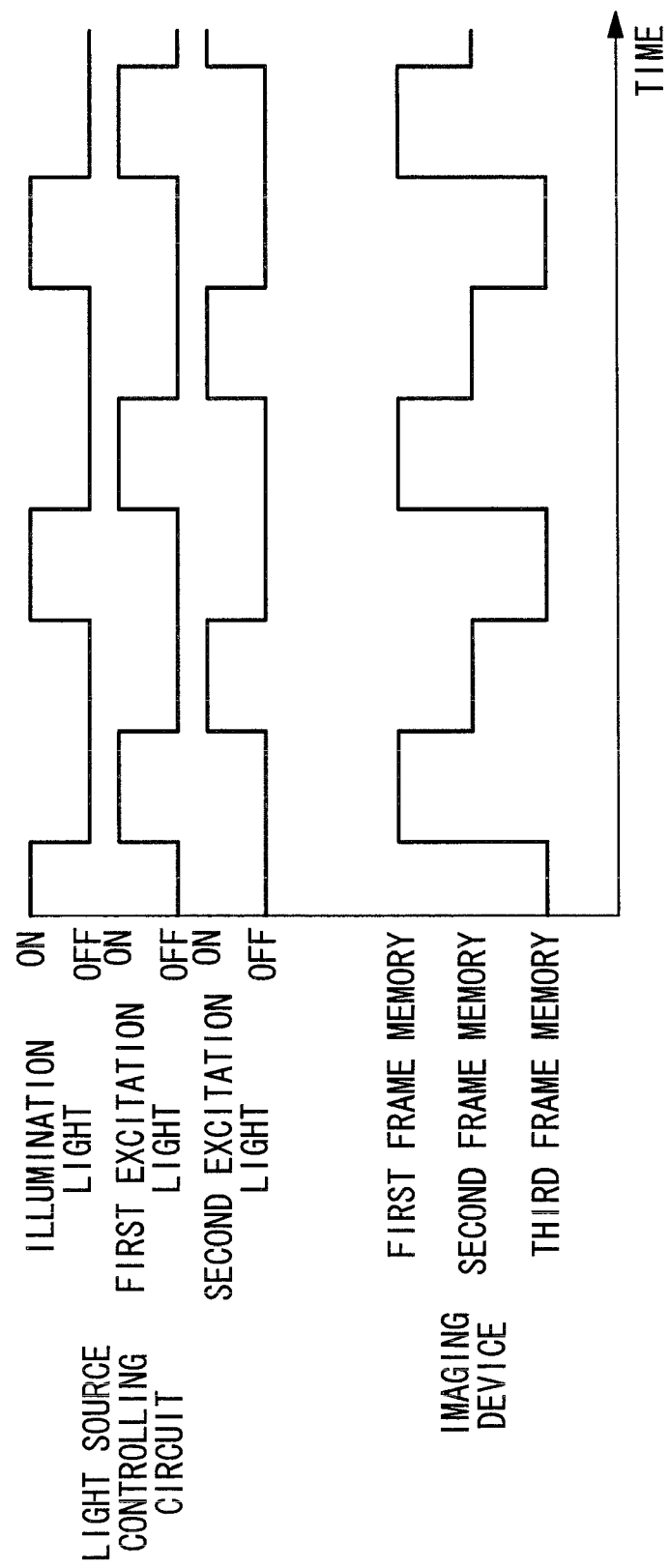
FIG. 4 is a timing chart for explaining the operation in the unmixing fluorescence observation mode of the endoscope system of FIG. 1.

On the other hand, when the unmixing fluorescence observation mode is selected, as shown in the timing chart of FIG. 4, by the operation of the light source controlling circuit 11, when the first excitation light is emitted from the excitation light source 10a, the imaging device driving circuit 15 outputs the image information which has been output from the imaging device 14, to the first frame memory 17a; while, when the second excitation light is emitted from the excitation light source 10b, the imaging device driving circuit 15 outputs the image information which has been output from the imaging device 14, to the second frame memory 17b.

In addition, when the illumination light is emitted from the illumination light source 9, the imaging device driving circuit 15 outputs the image information which has been output from the imaging device 14, to the third frame memory 17c. At this time, the blue (B) illumination light is irradiated as the illumination light by the operation of the color filter.

Moreover, the image processing circuit 18 receives the first fluorescence image information acquired by irradiation of the first excitation light and the second fluorescence image information acquired by irradiation of the second excitation light respectively from the first and second frame memories 17a and 17b, and performs the computation processing thereof. The computation processing in the image processing circuit 18 is performed in the following manner.

That is to say, the fluorescence intensities per unit concentration yielded from the AlexaFluor (trademark) 680-based fluorescent probe and the AlexaFluor (trademark) 700-based fluorescent probe when irradiated with the first excitation light are respectively assumed to be a and b, while the fluorescence intensities per unit concentration yielded from the AlexaFluor (trademark) 680-based fluorescent probe and the AlexaFluor (trademark) 700-based fluorescent probe when irradiated with the second excitation light are respectively assumed to be c and d.

The fluorescence intensity of a certain region by irradiation of the first excitation light is assumed to be P1, the fluorescence intensity of the same region by irradiation of the second excitation light is assumed to be P2, and the concentrations of the AlexaFluor (trademark) 680-based fluorescent probe and the AlexaFluor (trademark) 700-based fluorescent probe are respectively assumed to be N1 and N2. Then, the relationship of the equation 1 can be obtained.

[Equation 1]

$$\begin{pmatrix} P1 \\ P2 \end{pmatrix} = \begin{pmatrix} a & b \\ c & d \end{pmatrix} \times \begin{pmatrix} N1 \\ N2 \end{pmatrix} \quad (1)$$

The fluorescence intensities P1 and P2 are measured results. By substituting these values into the equation 1, the concentrations N1 and N2 of the respective fluorescent probes can be calculated.

The factors a, b, c, and d in the equation 1 can be previously obtained by measurement or the like, and may be input into the computation processing circuit by using the input device 19. Alternatively, values previously obtained by measurement or the like may also be stored in a memory storage (not shown) in the production unit during the production process.

As a result of the calculation, the thus output concentrations N1 and N2 of the respective fluorescent probes are respectively output to the first (for example, red) and second (for example, green) channels of the display unit. In addition, the image processing circuit 18 receives the reflected light image information acquired by irradiation of the illumination light, from the third frame memory 17c, and outputs the image information to the third (for example, blue) channel of the display unit 7.

The liquid delivery unit 5 comprises a first tank 21a for storing a washing liquid for washing the observation target, second and third tanks 21b and 21c for storing the first and second fluorescent probe solutions, the valves 20a, 20b, and 20c for selectively supplying/stopping the solutions from these tanks 21a, 21b, and 21c, a liquid delivery tube 22 connected to these valves 20a to 20c for supplying the respective solutions along the insertion section 2 to the distal end 2a, and the valve controlling circuit 16 disposed in the control unit 6 for controlling the valves 20a to 20c. The liquid delivery tube 22 has its distal end 22a disposed in the distal end 2a of the insertion section 2 so that the delivered washing liquid or fluorescent probe solution can be sprayed towards the observation target. As for the liquid delivery tube 22, a forceps channel provided in the insertion section 2 may be utilized, too.

Hereunder is a description of the operation of the thus configured endoscope system 1 according to this embodiment.

Figure 5A:
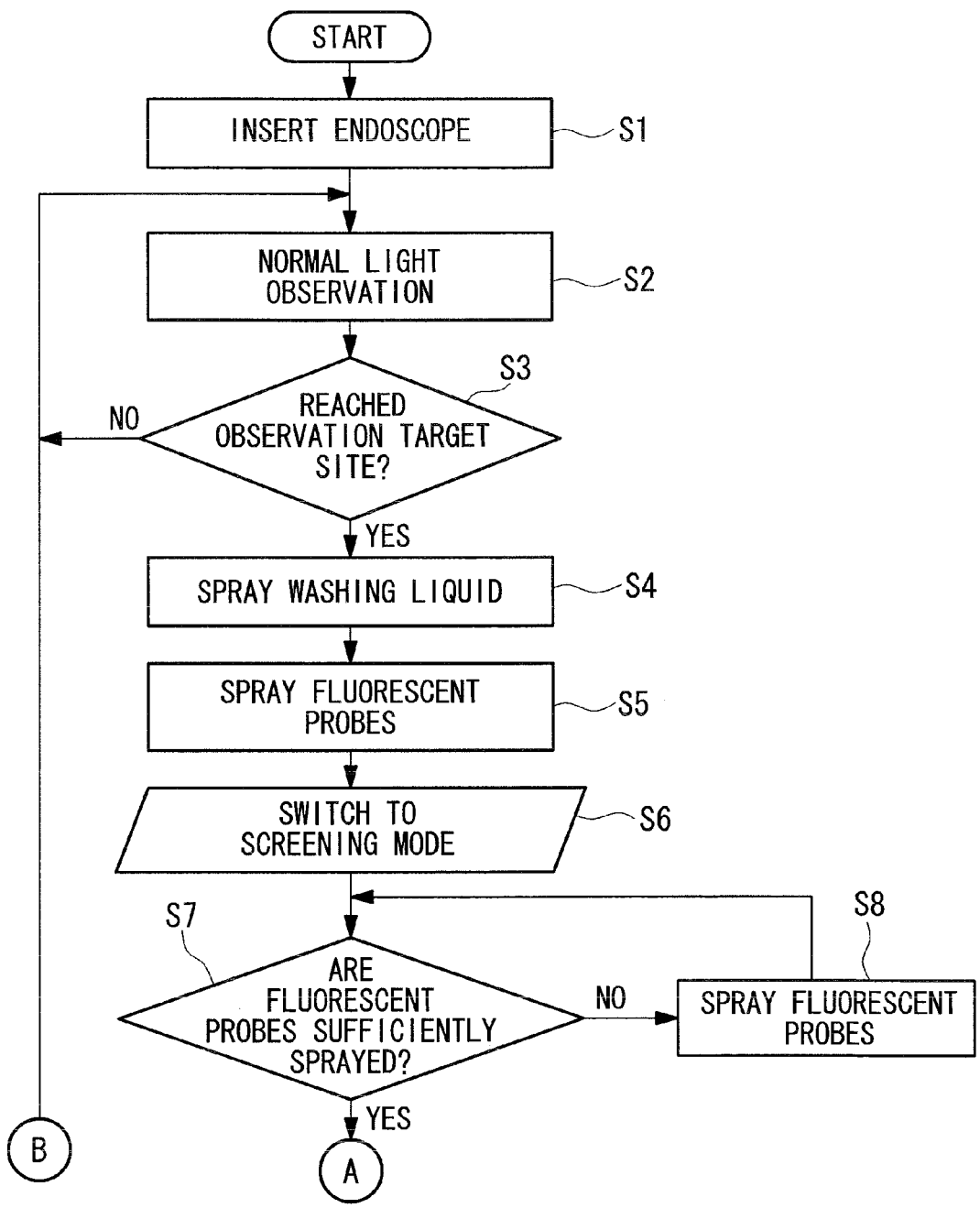
FIG. 5A is a flowchart for explaining the endoscopic observation procedure in a body cavity of an organism with use of the endoscope system of FIG. 1.
Figure 5B:
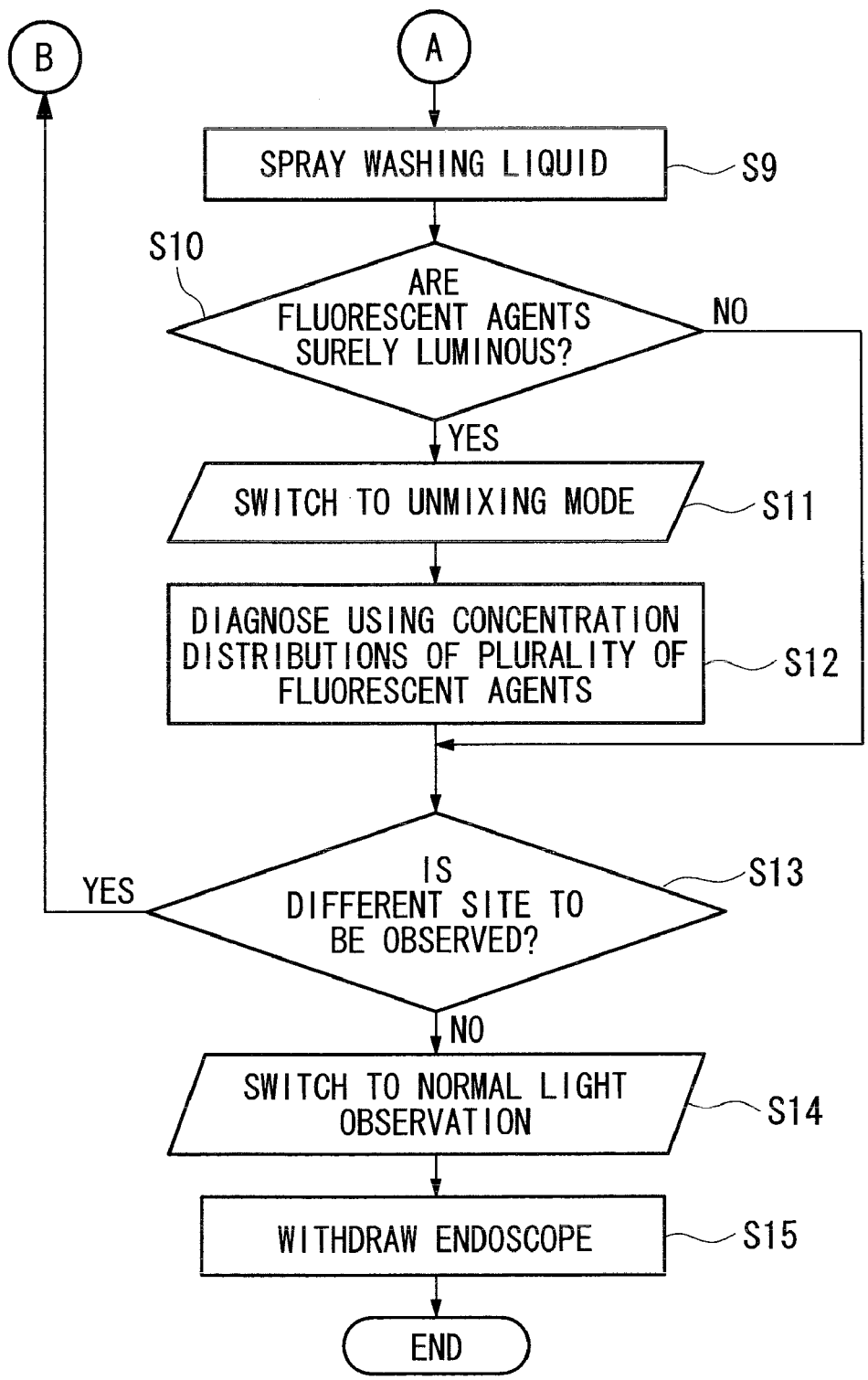
FIG. 5B is a flowchart for explaining the endoscopic observation procedure in the body cavity of the organism with use of the endoscope system of FIG. 1.

In order to capture the image of the observation target in a body cavity of an organism using the endoscope system 1 according to this embodiment, the image-taking is performed while switching the observation mode in accordance with the flowcharts shown in FIG. 5A and FIG. 5B.

That is to say, during the time when the insertion section 2 is being inserted in the body cavity (step S1), and is being guided to the site to be observed, the image-taking is performed by the normal light observation mode (step S2).

Since the observation is done by the normal light observation mode, the observation can be achieved with a brighter image than the fluorescence image, during the time when the endoscope is being inserted without a need of diagnosis using the fluorescence image. Also, the position of the observation target in the body cavity can be readily understood, and the observation target can be readily found in the field of view.

When the insertion section 2 has reached the observation target (step S3), and when the observation target is found in field of view, the user instructs to operate the valve controlling circuit 16 to perform the opening/closing operation of the valves 20a, 20b, and 20c.

That is to say, in a state where the illumination light source 9 irradiates the illumination light, the valve 20a is opened to discharge the washing liquid stored in the first tank 21a, from the distal end 22a of the liquid delivery tube 22 towards the observation target, to thereby wash the surface of the observation target (step S4).

In this case, according to this embodiment, since the observation target is washed in a state where the illumination light source 9 irradiates the illumination light, the affected part can be readily checked, and washing can be performed while ensuring the site to be sprayed with the fluorescent probe solution.

Moreover, the fluorescent probe solutions are also sprayed in a state where the illumination light source 9 irradiates the illumination light. Accordingly, the second and third valves 20b and 20c can be opened while ensuring the position of the washed observation target, and therefore small amounts of the fluorescent probe solutions can be exactly sprayed over the necessary site without missing the position of the observation target (step S5). By so doing, wasteful use of the expensive fluorescent probes can be prevented.

After the fluorescent probe solutions have been sprayed, the observation mode is switched to the screening fluorescence observation mode (step S6). By so doing, the operation to ensure that the fluorescent probes have been sufficiently sprayed all over the observation target in the fluorescence image, can be performed (step S7). If the spraying is insufficient, the fluorescent probes can be sprayed again (step S8).

After the fluorescent probes have been sufficiently sprayed, the valve 20a is opened to discharge the washing liquid stored in the first tank 21a, from the distal end 22a of the liquid delivery tube 22 towards the observation target, to thereby wash the surface of the observation target (step S9). By this washing operation, the fluorescent probes adhered to the surface of the observation target can be washed and removed, and only the fluorescent probes bound to the lesioned part can remain. After this washing operation, the pertinent sprayed region is observed in the screening fluorescence observation mode.

In the screening fluorescence observation mode, the blue illumination light and the first excitation light generated by the light source unit 4 are transmitted to the distal end 2a of the insertion section 2 respectively through the light guide 8, and are irradiated from the distal end 2a of the insertion section 2 towards the observation target.

When the first excitation light is irradiated on the observation target, two types of fluorescent probes permeated into the observation target are simultaneously excited. Then, the two types of fluorescence generated from the observation target are condensed by the imaging optical system 12, transmitted through the excitation light cut filter 13, then captured by the imaging device 14, and stored in the first frame memory 17a.

In this case, the excitation light irradiated on the observation target is partially reflected by the observation target and is incident into the imaging unit 3 together with the fluorescence. However, the imaging unit 3 is provided with the excitation light cut filter 13, and thus the excitation light is blocked and kept from being incident into the imaging device 14.

When the blue illumination light is irradiated on the observation target, the reflected light from the observation target is condensed by the imaging optical system 12, captured by the imaging device 14, and stored in the third frame memory 17c. At this time, since the excitation light cut filter 13 has a characteristic to transmit light in the wavelength band of the illumination light, the reflected light image is not affected.

In the screening fluorescence observation mode, the image processing circuit 18 outputs both the fluorescence image and the reflected light image to the display unit 7 without applying any processing, and presents the superposed image of the fluorescence image and the reflected light image.

As a result, if at least either one of the two types of fluorescent probes is luminous, the site can be recognized as a highly possibly lesioned site. In addition, since the reflected light image can also be simultaneously observed, the position of this site can be readily specified.

At this time, although the colors of the plurality of fluorescent probes are mixed in the fluorescence image, the image can be displayed as a noiseless and clear image since the exposure time is long and the noise is not amplified by the computation processing.

In addition, when the image-taking is performed while the insertion section 2 is relatively moved to the observation target, if the images of the respective excitation lights are taken at different timings, the computation is performed between images of different areas, by which the computation between these images may be expanded as noise. However, in the screening fluorescence observation mode, since the image-taking is continuously performed without switching the excitation light, such inconvenience will not happen.

As a result of the observation by the screening fluorescence observation mode, if no site is luminous by the fluorescent agents, the observation mode is again switched to the normal light observation mode, and then the endoscope is moved to a different observation target site.

In addition, as a result of the observation by the screening fluorescence observation mode, if there is a luminous site by the fluorescent agents (step S10), the observation mode is switched to the unmixing observation mode (step S11), and the site is subjected to intensive fluorescence observation with the plurality of fluorescent agents in a separate manner, by which the observation can be performed with images with higher diagnosability (step S12).

In the unmixing fluorescence observation mode, the illumination light, the first excitation light, and the second excitation light generated by the light source unit 4 are transmitted to the distal end 2a of the insertion section 2 respectively through the light guide 8, and are irradiated from the distal end 2a of the insertion section 2 towards the observation target.

When the first excitation light is irradiated on the observation target, two types of fluorescent probes permeated into the observation target are simultaneously excited. Then, as shown in FIG. 2, the two types of fluorescence are simultaneously generated from the observation target. These two types of fluorescence generated from the observation target are condensed by the imaging optical system 12 of the imaging unit 3, transmitted through the excitation light cut filter 13, and captured by the imaging device 14.

As for the imaging device 14, there is employed a device having a light-receiving sensitivity over a wide wavelength band of not less than 400 nm and not more than 900 nm. Therefore, the two types of the generated fluorescence are captured by the imaging device 14 in a superposed state, and the fluorescence image in a mixed-color state can be acquired.

In this case, the first excitation light irradiated on the observation target is partially reflected by the observation target and is incident into the imaging unit 3 together with the fluorescence. However, the imaging unit 3 is provided with the excitation light cut filter 13, and thus the first excitation light is blocked and kept from being incident into the imaging device 14.

Then, the fluorescence image information acquired by the imaging device 14 is stored in the first frame memory 17a.

Next, when the second excitation light is irradiated on the observation target, the two types of fluorescent probes permeated into the observation target are excited to generate fluorescence as shown in FIG. 2. The fluorescence generated from the observation target are condensed by the imaging optical system 12 of the imaging unit 3, transmitted through the excitation light cut filter 13, and captured by the imaging device 14.

In this case, the imaging device 14 acquires the fluorescence image information in a mixed-color state where the two types of fluorescence generated from the two types of fluorescent probes are superposed, while the second excitation light reflected by and returning from the observation target is blocked by the excitation light cut filter 13 and kept from being incident into the imaging device 14.

Then, the fluorescence image information acquired by the imaging device 14 is stored in the second frame memory 17b.

Furthermore, when the blue illumination light is irradiated on the observation target, the reflected light from the observation target is condensed by the imaging optical system 12, captured by the imaging device 14, and stored in the third frame memory 17c. At this time, since the excitation light cut filter 13 has a characteristic to transmit light in the wavelength band of the illumination light, the reflected light image is not affected.

At this time, the image processing circuit 18 receives the fluorescence image information made of the first and the second excitation light, from the first and second frame memories 17a and 17b, and performs computation on the basis of the equation 1 to respectively calculate the concentrations N1 and N2 of the AlexaFluor (trademark) 680-based fluorescent probe and the AlexaFluor (trademark) 700-based fluorescent probe.

In this unmixing observation mode, the concentration information of each fluorescent probe can be individually computed on the basis of the fluorescence image information acquired in a mixed-color state. Accordingly, without using a special element such as a variable spectral element, distributions of cancer cell-related molecules made by the respective fluorescent probes can be readily observed on the basis of fluorescence of wavelength bands adjacent or overlapped to an unseparatable degree even with the precise control of the variable spectral element.

The concentration information N1 and N2 calculated by the image processing circuit 18 are respectively output to the first and second channels of the display unit 7, and the reflected light image information is output to the third channel. These information are superposed and displayed on the display unit 7.

By so doing, the individual images showing the distributions of cancer cell-related molecules made by the respective fluorescent probes are displayed in a superposed state on the display unit 7.

As a result, when fluorescence are generated by two fluorescent probes from a same region, it can be readily ensured that cancer cells are highly likely present in the region. Moreover, it can also be determined that cancer cells are highly unlikely present in a region where fluorescence is generated only by either one of the fluorescent probes. By so doing, the actual external image of the observation target made by the illumination light can be displayed together with the image showing the distributions of cancer cell-related molecules made by the respective fluorescent probes in a superposed manner. Therefore, the region where cancer cells are highly likely present can be observed by corresponding to the actual external image of the observation target.

After the observation in the unmixing observation mode, if a different observation target site is observed (step S13), the flow goes back to the step S2 again, and the mode is switched to the normal light observation mode. Then, the endoscope is moved to the different observation target site, and the fluorescence image can be diagnosed in the same manner.

In addition, after the observation has been done all over the observation target site, the mode is switched to the normal light observation mode (step S14), and the endoscope is withdrawn from the body cavity of the organism. The observation can be achieved with a brighter image than the fluorescence image, during the time when the endoscope is being withdrawn without a need of diagnosis using the fluorescence image. Also, the position of the observation site in the body cavity can be readily understood, and the insertion section of the endoscope can be readily and safely withdrawn (step S15).

As described above, with the endoscope system 1 of the present invention, a noiseless and clear fluorescence image of a site of interest can be precisely made in a short time by selective use in accordance with the need of the user between the observation mode in which the concentration information of each fluorescent agent is presented by computation processing of the fluorescence intensity image, and the observation mode in which the fluorescence image is presented without performing the computation processing.

Particularly, by using the observation mode in which the fluorescence image is presented without computation processing prior to the observation mode in which the concentration information of each fluorescent agent is presented by computation processing of the fluorescence intensity image, the site of interest can be checked in a noiseless fluorescence image. By checking the site of interest in such a clear fluorescence image, the diagnosis can be efficiently performed in a short time.

On the other hand, when the illumination light is irradiated on the observation target, the illumination light is reflected by the surface of the observation target, condensed by the imaging optical system 12, and transmitted through the excitation light cut filter 13. Then the reflected light transmitted through the excitation light cut filter 13 is incident into the imaging device 14, and the reflected light image information is acquired. The acquired reflected light image information is stored in the third frame memory 17c, output to the third channel of the display unit 7 by the image processing circuit 18, and displayed by the display unit 7.

Moreover, in the endoscope system 1 according to this embodiment, since the wavelengths of the excitation lights are set on the longer wavelength side than the near infrared region, autofluorescent substances originally existing in the observation target will not be excited. Therefore, an advantage is given in which the generation of autofluorescence can be prevented and a clearer image can be acquired.

Furthermore, in this embodiment, the observation target is irradiated with the two types of the excitation lights and the illumination light, so that the image showing the concentration distributions of the fluorescent probes and the reflected light image are displayed in a superposed state. However, a third fluorescent probe may be used instead of the illumination light, and third excitation light for exciting the third fluorescent probe may be irradiated.

At this time, a fluorescent probe which generates fluorescence in a wavelength band differing from the wavelengths of fluorescence generated by the first and second fluorescent probes is used as the third fluorescent probe, by which the observation can be performed with more improved diagnosability with use of three types of fluorescent probes without causing color-mixture.

Alternatively, in this embodiment, the observation target is irradiated with the two types of the excitation lights and the illumination light, so that the image showing the concentration distributions of the fluorescent probes and the reflected light image are displayed in a superposed state. However, instead of the illumination light, third excitation light for generating the autofluorescence may be irradiated on the observation target.

Since the autofluorescence has a wavelength band apart from those of the fluorescence of the agents set in the near infrared region, it can be detected without color-mixture with the fluorescence of the agents.

The invention claimed is:

1. An endoscope system at least a part of which can be inserted into a body cavity of an organism for capturing an image of an observation target in the body cavity, comprising:
    a light source section for selectively irradiating two or more types of excitation lights having different spectral characteristics so as to excite two or more types of fluorescent agents having different optical characteristics;
    an imaging section provided on the part to be inserted into the body cavity, having a filter which cuts the respective excitation lights, and having a light-receiving sensitivity in the wavelength bands of the two or more types of fluorescences radiated from the observation target by the respective excitation lights;
    a storage section for storing relation information between the fluorescence intensity generated by excitation with each of the excitation lights and the concentration of each of the fluorescent agents;
    a concentration information computing section for computing concentration information of each of the fluorescent agents on the basis of the fluorescence intensities of two or more images captured by the imaging section and the relation information stored in the storage section, and outputting the concentration information; and
    a mode switching section capable of switching between a first fluorescence observation mode in which at least one of the fluorescence intensity images acquired by the imaging section is presented, and a second fluorescence observation mode in which the concentration information of each of the fluorescent agents computed by the concentration information computing section is presented.

2. An endoscope system according to claim 1, wherein said mode switching section switches the observation mode to said first fluorescence observation mode prior to said second fluorescence observation mode.

3. An endoscope system according to claim 1, wherein said relation information is information on a ratio between the fluorescence intensity generated by excitation with each of the excitation lights and the concentration of each of the fluorescent agents.

4. An endoscope system according to claim 1, comprising a display section for displaying the concentration information that has been computed and output by said concentration information computing section.

5. An endoscope system according to claim 4, wherein said display section comprises a plurality of channels corresponding to display colors, and
    the concentration information corresponding to each of the fluorescent agents is allocated to each channel to be output.

6. An endoscope system according to claim 1, wherein the wavelengths of the respective excitation lights are set on the longer wavelength side than the near infrared region.

* * * * *